United States Patent [19]

Kiechel et al.

[11] Patent Number: 5,169,849
[45] Date of Patent: Dec. 8, 1992

[54] NASAL PHARMACEUTICAL COMPOSITIONS

[75] Inventors: Jean-René Kiechel, Rueil-Malmaison; Francoise, Acézat-Mispelter, Elancourt; Danielle Plas, Rueil-Malmaison, all of France

[73] Assignee: Sandoz Ltd., Basel, Switzerland

[21] Appl. No.: 603,990

[22] Filed: Oct. 26, 1990

Related U.S. Application Data

[63] Continuation of Ser. No. 428,086, Oct. 27, 1989, abandoned, which is a continuation of Ser. No. 229,036, Aug. 5, 1988, abandoned, which is a continuation of Ser. No. 922,639, Oct. 24, 1986, abandoned, which is a continuation of Ser. No. 725,579, Apr. 22, 1985, abandoned, which is a continuation of Ser. No. 625,717, Jun. 28, 1984, abandoned, which is a continuation of Ser. No. 462,813, Feb. 1, 1983, abandoned.

[30] Foreign Application Priority Data

Feb. 1, 1982 [GB] United Kingdom ............ 8202781

[51] Int. Cl.⁵ .................. A61K 31/50; A61K 31/495
[52] U.S. Cl. .................. 514/250; 514/263; 514/947
[58] Field of Search .......... 514/250, 263, 947

[56] References Cited

U.S. PATENT DOCUMENTS 4,165,376  8/1979  Rosenberg .................. 514/325

FOREIGN PATENT DOCUMENTS 1043842  9/1966  United Kingdom .

OTHER PUBLICATIONS

Chemical Abstracts 91:198,943e (1979).

*Primary Examiner*—Leonard Schenkman
*Attorney, Agent, or Firm*—Gerald D. Sharkin; Robert S. Honor; Carl W. Battle

[57] ABSTRACT

A nasal pharmaceutical composition incorporates a non-toxic agent which is capable of increasing the ciliary function e.g. caffeine and at least partially antagonizing the ciliary function depressant effect of the active agent e.g. dihydroergotamine or any other constituent present in the composition.

31 Claims, No Drawings

NASAL PHARMACEUTICAL COMPOSITIONS

This is a continuation of application Ser. No. 07/428,086, filed Oct. 27, 1989 now abandoned, which in turn is a continuation of application Ser. No. 07/229,036 filed Aug. 5, 1988 now abandoned, which in turn is a continuation of application Ser. No. 06/922,639 filed Oct. 24, 1986, now abandoned, which in turn is a continuation of application Ser. No. 06/725,579 filed Apr. 22, 1985, now abandoned, which in turn is a continuation of application Ser. No. 06/625,717 filed Jun. 28, 1984, now abandoned, which in turn is a continuation of application Ser. No. 06/462,813 filed Feb. 1, 1983, now abandoned.

This invention relates to nasal pharmaceutical compositions.

The practice of nasally administering some pharmacologically active agents such as broncholytics and hormones to attain systemic absorption has been known for a long time [see pages 722-729 in "Pharmazeutische Technologie" edited by H. Sucker, P. Fuchs and P. Speiser, Georg Thieme Verlag, Stuttgart, 1978]. Nasal systemic administration of pharmacologically active agents may offer significant advantages over other routes of administration. For example, after passing through the nasal mucous membrane the active agent enters the blood stream directly, thus leading to immediate bioavailability of active agent in the blood and a rapid onset of therapeutic action. Nasal aerosol applicators capable of providing a precise dose of the active agent in liquid or powder spray form of suitable droplet or particle size for nasal administration are available which are easy to use. However, the nasal route of systemic administration of pharmacologically active agents is still uncommon.

UK Patent Specification Number 1,592,563 discloses that certain ergot cyclic peptide alkaloids may be beneficially administered by the nasal route. Nasal pharmaceutical compositions of dihydroergotamine, in particular in the form of liquids and powders, are disclosed which can be used to provide a suitable spray. A representative nasal pharmaceutical composition contemplated by the above mentioned Patent Specification is an aqueous solution containing per ml 4 mg dihydroergotamine mesylate, 50 mg ethanol and 150 mg glycerine, and this composition is hereinafter referred to as the "reference" solution.

Often pharmaceutical compositions formulated for nasal administration turn out to be unsatisfactory in wide-spread clinical use. For example they may be unstable over a long period of time, not well tolerated or not well accepted by patients. An important factor for bad tolerance may be that a constituent of the composition, perhaps the active agent, depresses the ciliary function.

The air passage cilia are microscopic hairlike structures about 7 microns in length and 1 to 3 microns in diameter. These cilia are on the surface layer of the mucus membrane in the nose and in the trachea. The cilia perform undulatory motions at a frequency beat of about 300-900 cycles per minute at 37° C. that propel mucus together with dust particles and other foreign matter towards the passages at the back of the nose (choanae) which communicate with the pharanx or forwards towards the nostril openings. The particles and matter are thus either swallowed or sneezed away. The mucus layer may move at a rate of about 2 to 10 mm per minute in some animals. Studies made by I. B. Andersen et al in American Review of Respiratory Disease 106, 438 (1977) an average mucus flow rate of 4.8 mm per minute was found in a group of humans. The individual flow rates varied from 0 to 23.6 mm per minute.

It will readily be appreciated that any substance that depresses the ciliary function interferes with one of the major protective mechanisms of the body.

The extent to which a nasally administered agent depresses the ciliary function may be observed in standard tests, e.g. in vitro, using the ciliary trachea of animals.

One reproducible and sensitive test is as follows:

The trachea or nasal septum of a guinea pig or rabbit is removed immediately after sacrifice. The organ is immersed in physiological balance serum (Dulbecco) at 23° C. A tubular fragment, e.g. of 3 tracheal rings, is removed and the ciliary epithelium is scraped therefrom. The beating frequency of cilia at one particular point is measured by microphoto-oscillographic techniques according to the principles of L. Chevance et al, Acta Otolaryng, 70, 16-28, (1970) wherein the cilia are observed and magnified 500 times. A change in beating frequency indicates a change in ciliary function.

Some pharmacologically active agents inparticular dihydroergotamine depress the ciliary function. Thus application (about 0.1 to 0.3 ml) of the "reference" solution or an aqueous solution containing 4 mg dihydroergotamine mesylate per ml to the cilia results in an irreversible depression of cilia beating within 2 minutes after application.

Moreover we have found that non-toxic agents which increase the ciliary function, in particular xanthines, e.g. which increase the ciliary beating frequency in the above test, may be used to at least partially counteract the ciliary function depressant effects of other constituents in a pharmaceutical composition, and provide clinically well tolerated nasal pharmaceutical compositions.

The present invention accordingly provides a nasal pharmaceutical composition incorporating a pharmacologically active agent, the active agent or any other constituent present being capable of inducing, as a side effect, the depression of ciliary function and also containing a non-toxic agent which is capable of increasing the ciliary function.

The present invention furthermore provides nasal co-administration of a pharmacologically active agent which is capable of depressing ciliary function and a non-toxic agent which is capable of increasing the ciliary function. The invention also provides a method of nasally administering a pharmacologically active agent which is capable of depressing ciliary function characterised by nasal co-administration with a non-toxic agent which is capable of increasing the ciliary function, e.g. onto the nasal mucus membrane. Furthermore, the invention provides a nasal pharmaceutical composition comprising dihydroergotamine and a non-toxic agent which is capable of increasing the ciliary function. Such nasal pharmaceutical compositions will be most preferably in the form of a liquid or a powder.

Agents which increase ciliary function may be determined by in vitro tests, e.g. the above mentioned test, and suitably produce a 20% or greater increase in ciliary function 20 minutes after administration. The choice of agent is not critical so long as it is pharmacologically acceptable. The amount of ciliary function increasing agent present in the composition will naturally depend on the amounts of other constituents which depress the ciliary function and the extent to which they depress the ciliary function. Preferred amounts of ciliary increasing agent in the nasal pharmaceutical composition may be determined by routine experimentation, e.g. using the above mentioned in vitro test.

A xanthine is especially effective in antagonising the depression of ciliary function, e.g. induced by a pharmacologically active agent. We have also found that such xanthines are well tolerated on nasal administration. Furthermore nasal pharmaceutical compositions containing such xanthines may be made which are liquid solutions stable against e.g. decomposition, precipitation out or discolouration at an acceptable pH, and which may be sterilized easily.

Accordingly in another aspect the present invention provides nasal co-administration of a xanthine with a pharmaceutically active agent which is capable of depressing ciliary function. In yet another aspect the present invention provides a method of nasally systemically administering a pharmacologically active agent which is capable of depressing ciliary function characterised by co-administration with a xanthine. In a further aspect the present invention provides a nasal pharmaceutical composition comprising a pharmacologically active agent which is capable of depressing ciliary function, and a xanthine.

The pharmacologically active agent may be for example an active agent which is capable of being systemically absorbed through the nasal mucus membrane and passing into the body circulation. The active agent should of course be non-toxic.

The present invention is particularly suitable for use with active agents which significantly depress ciliary beating in the in vitro test as described above, e.g. show a 50% or greater reduction of ciliary beating 20 minutes after application of the dose of active agent.

As indicated above the pharmacologically active agent is preferably an ergot cyclic peptide alkaloid product disclosed as formula I in UK Patent Specification Number 1,592,563, the contents of which are hereby incorporated by reference, and is especially dihydroergotamine.

The active agent may be administered in free base form or in pharmaceutically acceptable acid addition salt form, e.g. the mesylate. Such salts in general have the same order of activity as the active agent. For example dihydroergotamine may be administered in the form of the mesylate.

The particular therapeutic effect exhibited by the pharmacologically active agent is not critical. In view of the rapid increase in active agent concentration in the blood after nasal administration, the nasal pharmaceutical compositions of the invention are specially suitable for administration of active agents for the treatment of conditions which require quick relief, e.g. particularly orthostatic hypotension and especially migraine.

The dosage of pharmacologically active agent to be administered will naturally vary from compound to compound. In general a satisfactory dosage is one which provides the same order of bioavailability or therapeutica effect as that obtainable by injecting a therapeutically effective amount of the active agent. Often the nasal route requires smaller dosages than the oral route to obtain the same effect e.g. a nasal dosage may be from about 0.5 to about 0.01 times the oral dose. For example with dihydroergotamine 1 mg administered nasally produces the roughly same quantitative effect (as indicated by bioavailability studies or vasocontriction of hand veins) as 10 mg dihydroergotamine administered orally. For dihydroergotamine the preferred amount to be administered nasally is in the order of from about 0.5 to 5 mg.

Naturally the dose of active agent should not be so high or the dosage repeated so often that side effects might occur.

The choice of xanthine is not critical. Any xanthine may be used, for example a xanthine of formula

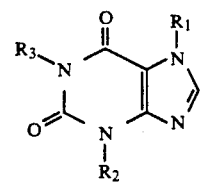

wherein $R_1$, $R_2$ and $R_3$ are chosen from hydrogen or alkyl ($C_{1-10}$).

Such xanthines are in general known. Examples of suitable xanthines include theophylline and the preferred xanthine is caffeine.

The exact amount of xanthine, or other agent capable of increasing the ciliary function, to be administered in a dose will depend, inter alia, on the extent to which the pharmacologically active agent and any other constituent present in the nasal pharmaceutical composition depresses the ciliary function. The ratio of active agent to xanthine or other ciliary increasing agent may vary within wide limits and may be determined by routine experimentation. A suitable ratio is from about 0.1:1 to about 10:1. It is preferred to use the minimum amount of xanthine or other agent capable of increasing the ciliary function to bring the ciliary function to within 50 to 100% of the base value (of untreated cilia) within 20 minutes after application in the above mentioned in vitro ciliary function test. Satisfactory results have been obtained with from about 2 mg to about 20 mg xanthine per dose.

The nasal composition may contain, e.g. about 0.2 to about 2%, more preferably 0.5% to 2%, by weight of xanthine, e.g. in a liquid of e.g. 4 mg dihydroergotamine per liter.

It is preferred to administer a nasal spray which is isotonic, or is slightly hypertonic, with respect to the ciliary mucus. Conveniently the osmotic pressure of liquid providing the spray is from about 200 to 600 mOsm, especially from 280 to 360 mOsm, per liter. The desired osmotic pressure may be obtained by the addition of any conventional non-toxic isotonizing agent. Sodium chloride may for example be used. Preferably a non-toxic sugar is used, especially glucose.

The exact amount of isotonizing agent to be present depends, inter alia, on the osmotic power of the particular isotonizing agent and the osmotic pressure of the other constituents in the nasal pharmaceutical composition. The weight ratio of xanthine or other agent capable of increasing the ciliary function to isotonizing agent may be, for example, from about 1:0.05 to about 1:10.

For a sugar, a typical amount is from about 10 mg to 100 mg per dose. The weight ratio of ciliary function increasing agent to sugar is for example from about 1:1 to about 1:10. This may correspond to about 1 to about 10%, e.g. 2.5 to 5%, for liquid compositions. For sodium chloride a suitable weight ratio of ciliary function increasing agent to sodium chloride is for example from about 1:0.5 to about 1:1. For liquid compositions a suitable concentration is from about 0.5 to about 0.9 per cent.

The nasal pharmaceutical composition of the invention may be in liquid form. A solvent such as water may be used. A co-solvent such as propylene glycol may be present, preferably in a concentration of less than 10% e.g. 0.1 to 10%. The composition is preferably in the form of an aqueous solution. Alternatively it may be in the form of a suspension or an oil-in-water emulsion.

If desired the nasal pharmaceutical composition of the invention may be in powder form. Preferably the powder is designed to dissolve rapidly on contact with the mucus membrane. The powder is conveniently amorphous, any crystals being present therein having an extremely small size.

If desired other nasal pharmaceutical excipients may be present. The exact choice of other excipients present will depend on a number of factors, including stability and tolerability of the resultant pharmaceutical compositions. The influence of several excipients have been described in the literature, e.g. in H. J. M. van de Donk et al. First European Congress of Biopharmacy and Pharmacokinetics Apr. 1-3, 1981, Editors J. M. Aiache and J. Hirtz, Clermont.Ferrant, p. 406-413. For example, an anti-oxidant such as benzoic acid, sodium metabisulphate or methyl parahydroxybenzoate or preferably benzalkonium chloride, cetylpyridinium chloride or phenododecinium bromide, or a protective gas such as carbon dioxide, may be present.

The weight ratio of anti-oxidant to ciliary function increasing agent is preferably kept very low, e.g. from about 0.2:1 to about 0.02:1. The concentration of antioxidant in a liquid may be for example from 0.2% to 2% o.

If desired a tenside may be present, such as sorbitan mono-oleate. Naturally the amounts of pharmaceutical excipients are conveniently kept as low as possible, e.g. in liquid form less than about 5% of the amount of xanthine or other agent capable of increasing the ciliary function in the composition.

When the nasal pharmaceutical composition is in solid form then an inert carrier may be employed, which may comprise for example from about 97.5 to 85% of the composition. Alternatively no inert carrier may be necessary.

The final pH of th nasal composition of the invention is preferably from about 3.8 to about 7, conveniently 3.8 to 4.5 in the case of dihydroergotamine.

The desired pH may be achieved by means of the presence of a buffer system, e.g. acetic acid/sodium acetate, $CO_2/HCO_3^-$, or $HPO_4^{--}/H_2PO_4^-$.

The nasal pharmaceutical compositions of the invention may be formulated in conventional manner, e.g. by admixture of the constituents e.g. to form a solution in water, if desired followed by filtering of the solution and/or sterilizing under conventional conditions, e.g. by heating. If a powder pharmaceutical composition is desired then preferably a lyophilizate is produced by exposing a chilled solution of the nasal pharmaceutical composition to a vacuum.

The nasal pharmaceutical compositions of the invention in use are conveniently packaged in conventional manner in a nasal spray applicator constructed to produce a spray of the composition. If desired pressure of a compressed gas, e.g. air, nitrogen or a hydrocarbon such as a freon or ultrasonic means may be used to provide the spray. The applicator may be constructed to receive a unit dosage form, e.g. an ampoule, capsule or the like containing a sufficient amount of the nasal pharmaceutical composition according to the invention for a single dose. Alternatively the ampoule may be of sufficient volume, e.g. 5 to 10 ml, to provide several doses of the nasal pharmaceutical composition. Numerous suitable nasal spray applicators are known, e.g. "Microcompack" from Aerosol Services AG, CH-4313 Moehlin, Switzerland, or applicators from Valois S.A., BG G-26110 Le Neubourg, France, both of which provide liquid sprays.

The ampoule may be broken before being inserted into the nasal spray applicator.

When the nasal pharmaceutical composition of the invention is liquid then the volume of composition to be dispensed in one dose may vary between wide limits. A suitable volume is from 0.1 to 0.2 ml. The particle size of the spray is preferably greater than 800 microns, e.g. in the range of from about 800 to 1000 microns.

When the nasal pharmaceutical composition of the invention is solid, the volume and particle size of composition to be administered in a single dose my be also vary within wide limits. Preferably the volume is in the range of about 0.1 ccm and the particle size is from about 800 to about 1000 microns.

For the preferred active agent dihydroergotamine the ratio of xanthine or other agent capable of increasing the ciliary function to active agent is conveniently from about 1:0.1 to about 1:1. Preferably the pharmaceutical composition is in the form of a solution containing from about 0.2 to about 2%, e.g. 0.5 to 2%, by weight of the xanthine or other agent capable of increasing the ciliary function. Conveniently glucose is present.

A particularly preferred nasal pharmaceutical composition of the invention contains an aqueous solution of 0.4% dihydroergotamine mesylate, 5% glucose and 1% caffeine. This composition is hereinafter referred to as composition A.

The muco-ciliary effect of caffeine in the nasal pharmaceutical compositions of the invention may be determined in conventional manner in standard in vitro and in vivo tests. One particularly appropriate in vitro test has been described above. Another test may be effected according to the principles of R. Guillerm, Il Farmaco, 1, 1-18 (1972). A piece of a sheep or rat trachea containing cilia and mucus is stretched on a thermostatically controlled plate at 35° C. The nasal pharmaceutical composition is sprayed onto the trachea by means of an ultrasonic aerosol delivering 1 ml of solution per liter of air per minute over a period of 5 minutes. The spray nozzle diameter is from 2 to 4 microns.

The ciliary beating frequency is measured by photo-oscillographic techniques, according to the principles of R. Guillerm et al., Physiol. 57, 725, (1965). In this test the composition A of the invention has a very small effect on the ciliary function.

An example of the results is:

| Composition | Time after administration | | | | | | |
|---|---|---|---|---|---|---|---|
| | 0 min | 5 min | 10 min | 20 min | 30 min | 60 min | 90 min |
| | Cilary beating frequency (cycles/minute) | | | | | | |
| 5% glucose | 420 | 480 | nt | nt | nt | 420 | nt |
| 1% caffeine | 340 | 380 | nt | 500 | nt | nt | 520 |
| 1% caffeine + glucose | 320 | 240 | 300 | 420 | 420 | nt | nt |

-continued

| | Time after administration | | | | | | |
|---|---|---|---|---|---|---|---|
| | 0 min | 5 min | 10 min | 20 min | 30 min | 60 min | 90 min |
| Composition | Cilary beating frequency (cycles/minute) | | | | | | |
| Composition A | 360 | nt | 380 | 300 | nt | nt | nt | nt = not tested

In a further in vitro test the speed of movement across a mucosal trachea piece from a sheep is studied according to the principles of S. P. Battista in Screening methods in Pharmacology, Editors R. A. Turner and P. Hebborn, Vol. 2, Academic Press, New York, 1971, 167–202. The trachea is maintained in a stretched condition in a thermoregulated chamber. The speed of movement of a particle across the mucus membrane is studied-including across an area of the trachea where ca. 0.1 to 0.2 ml of the nasal pharmaceutical composition has been sprayed.

An example of results obtained with composition A of this invention is as follows:

| | Run 1 | | Run 2 | |
|---|---|---|---|---|
| Time (minutes) | Distance travelled (mm) | speed (mm/min) | Distance travelled (mm) | speed (mm/min) |
| 0 | Spray of 130 microliters of composition A into a zone 1 cm broad and crossed at about 12 minutes after the start from which the particle departs | | | |
| 5 | 38 | 7.6 | 50 | 10 |
| 7 | 52 | 7 | 70 | 10 |
| 9[1] | 70 | 9 | 90 | 10 |
| 12[2] | 83 | 4.3 | 110 | 6.7 |
| 15[3] | 110 | 9 | 140 | 10 |

[1] approach to sprayed area;
[2] crossing of sprayed area;
[3] departure away from sprayed area As can be seen there is only a slight reduction in speed of the particle when it is crossing over the zone treated with composition A.

The muco-ciliary properties of the nasal pharmaceutical composition of the invention may also be observed in in vivo tests.

A clinical test was effected to measure the nasal drainage in accordance with the principles of I. Andersen et al., Am. Rev. Respir. Dis. 110, 301–305 (1974). In one trial a grain of saccharin (0.4 to 0.6 mm in diameter) is placed on the nasal mucus membrane of healthy volunteers, in the region of the middle concha in front of the upper nasolacrinal duct where the nostrils are the most permeable. The time taken for a subject to experience a a sweet sensation is recorded as th mucociliary transport time.

About 0.13 ml of a nasal pharmaceutical composition is sprayed into the nose. The grain of saccharin is placed into the nose 3 minutes later. 5 minutes later the subjects are asked every 30 seconds whether a sweet sensation has been observed. The mean results obtained in 12 subjects were as follows:

| | Time of transit[5] (minutes) | |
|---|---|---|
| Placebo[4] | 15.2 | ±4.7 |
| Composition A | 13.9 | ±2.6 |

[4]NaCl 9°/oo aqueous solution
[5]Period from spraying until experience of sweetness Composition A slightly decreased the transit time but not significantly. The composition was in general well tolerated. A slight transitory prickling sensation in the nasal mucosa was observed by one subject out of 12 on placebo and 2 subjects out of 12 with composition A.

In another preliminary trial the "reference" solution was used. Results obtained were:

| | Time of transit[5] (minutes) | |
|---|---|---|
| Placebo[4] | 15.44 | ±3.86 |
| Reference | 22.50 | ±10.12 |

For meanings of [4] and [5] see above

An undesirable 40 to 45% increase in the transit time was observed. 4 out of the ten subjects experienced irritation. 3 out of 10 subjects experienced vasomotor disorders (rhinorrhea and obstruction).

Moreover, even when the nasal mucus membrane is challenged with a nasal pharmaceutical composition of the invention in sufficient quantities to provide a therapeutic effect the amount of xanthine absorbed may be low. For example in one double-blind clinical trial, a nasal spray of compostion A was administered to ten healthy volunteers. The equivalent of 2.6 mg caffeine was administered. The amount of caffeine detected in the blood in one preliminary trial was as follows:

| | | |
|---|---|---|
| Area Under Curve | (nanogram/ml/hr) | 22.29 ± 3.94 |
| Cmax | (nanogram/ml) | 2.34 ± 0.52 |

The amount of caffeine detected in the body was thus ten to twenty times less than that expected from drinking a cup of coffee (containing e.g. 50 to 100 mg caffeine).

The efficacy of the compositions according to the invention may be determined in conventional clinic therapeutic trials. For example with composition A a clinical study has been effected in patients suffering from migraine.

The study was effected with a composition A and placebo in 9 patients according to a double blind cross-over plan. Each patient was treated for 1 month with either composition A or placebo.

Spray applicators designed to administer a metered dose of 0.5 mg dihydroergotamine in the form of composition A or a similar volume of placebo solution were used. At the beginning of a migraine attach each subject administered a metered dose into each nostril. Every 30 minutes a further dose is administered if the attack persists up to a maximum of 4 doses within 24 hours.

7 subjects out of 9 when treated with composition A experienced a beneficial effect on the migraine attack. With placebo only 1 patient obtained some beneficial effect. Further data obtained in this trial were:

| | Treatment | |
|---|---|---|
| | Composition A | Placebo |
| Total number of migraine attacks | 41 | 26 |
| Results | | |
| Alleviation of attack | 22 | 0 |
| Decrease in intensity of attack | 5 | 6 |
| No effect | 14 | 20 |

These results show a statistically significant beneficial effect of composition A on the migraine attack.

On a global assessment, the tolerance of composition A was excellent in 8 subjects and acceptable in 1 patient.

As indicated above the nasal pharmaceutical compositions of the invention are stable. The stability can be measured in standard stress stability tests wherein the active agent concentration is determined. An example of results obtained with composition A and the "reference" solution is as follows:

| Temperature Weeks | Reference Solution | | | Composition A | | |
|---|---|---|---|---|---|---|
| | 35° C. | 44° C. | 50° C. | 35° C. | 44° C. | 50° C. |
| | Concentration % | | | Concentration % | | |
| 0 | 104 | 104 | 104 | 103 | 103 | 103 |
| 3 | 99 | 96 | 92 | 102 | 94 | 93 |
| 6 | 97.5 | 90.5 | 83.5 | 103 | 92 | 88 |
| 9 | 93 | 86 | 76 | 101 | 89 | 85 |

As indicated by the above results composition A is overall significantly more stable than the reference solution. In further trials the lyophilisate of composition A was shown to have excellent stability even at 50° C.

In another stability trial a piston nasal spray applicator fitted to a bottle filled with 10 ml of composition A or the reference solution was used to produce a nasal spray of 0.13 ml, 11, 21, 31, 61 and 91 days after filling. After a spray has been produced air is sucked into the bottle to replace the sprayed solution, and hence the air may induce decomposition.

With composition A the concentration of dihydroergotamine was about 89% the original value after 91 days. With the reference solution at 61 days the concentration of dihydroergotamine was 81% the original value and at 91 days 66% the original value.

Thus the stability of composition A is significantly better than the reference solution.

As used herein all percentages and weight ratios refer to parts by weight except percentages referring to liquids when they refer to weight per volume of liquid.

The following Example illustrates the invention:

EXAMPLE 1

| 1. Composition | | |
|---|---|---|
| Constituents | per 1 ml | per 10 liters |
| Dihydroergotamine mesylate | 0.004 g | 40 g |
| Caffeine | 0.010 g | 100 g |
| Glucose | 0.050 g | 500 g |
| Water to | 1 ml | 10 l |

2. Preparation of the composition 9 liters of water are saturated with carbon dioxide. 100 g of caffeine are dissolved in the water and then 40 g dihydroergotamine mesylate. 500 g Glucose are dissolved in the stirred solution, without stopping saturation with carbon dioxide. Water is added to 10 liters. The mixture is filtered in the presence of carbon dioxide through a filter (0.22 micron holes).

3. Filling of ampoules

Ampoules are filled with a maximum of 1 ml solution under carbon dioxide, sealed and then are sterilized in an autoclave at 121° C. for 5 minutes. The pH is typically between 4.38 and 4.46 at 22° C.

4. Use

The ampoules are broken open and then inserted into a conventional nasal dispenser. The dispenser sprays for each dose about 0.13 ml of solution containing 0.5 mg of dihydroergotamine. The dose is applied nasally 2 to 4 times a day in the prophylaxis or treatment of migraine.

What we claim is:

1. A liquid nasal pharmaceutical composition containing as an active agent a pharmaceutically effective amount of dihydroergotamine which is capable of depressing the ciliary function and an effective amount of a xanthine which is capable of increasing the ciliary function, wherein the weight ratio of said dihydroergotamine to said xanthine is about from 0.1:1 to 10:1.

2. A composition according to claim 1 wherein the dihydroergotamine present is in the form of the mesylate.

3. A composition according to claim 1 wherein the xanthine is of formula

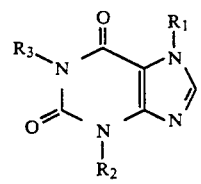

wherein $R_1$, $R_1$ and $R_3$ are chosen from hydrogen or alkyl ($C_{1-10}$).

4. A composition according to claim 3 wherein the xanthine is theophylline.

5. A composition according to claim 3 wherein the xanthine is caffeine.

6. A composition according to claim 5 containing a non-toxic isotonizing agent.

7. A composition according to claim 6 wherein the weight ratio of agent capable of increasing the ciliary function to isotonizing agent is from 1:0.05 to 1:10.

8. A composition according to claim 6 wherein the isotonizing agent is a sugar.

9. A composition according to claim 8 wherein the sugar is glucose.

10. A composition according to claim 9 wherein the weight ratio of ciliary function increasing agent to glucose is from 1:1 to 1:10.

11. A composition according to claim 1 in the form of a solution.

12. A composition according to claim 1 wherein the osmotic pressure is from 280 to 360 mOsm per liter.

13. A composition according to claim 1 in unit dosage form saturated with carbon dioxide gas.

14. A composition according to claim 1 in a nasal spray applicator.

15. A composition according to claim 14 wherein the spray applicator is designed to produce a spray of droplet size 800 to 1000 microns in diameter.

16. A nasal pharmaceutical composition comprising dihydroergotamine mesylate and caffeine in a weight ratio of 1:0.1 to 1:1 and glucose.

17. A method of nasally systemically administering a pharmaceutically effective amount of dihydroergotamine which is capable of depressing the ciliary function comprising nasally co-administering an effective amount of a xanthine which is capable of increasing ciliary function, wherein the weight ratio of said dihydroergotamine to said xanthine is about from 0.1:1 to 10:1.

18. A method according to claim 17 of treating hypotension or migraine.

19. A method of claim 17 wherein the dihydroergotamine is in the form of the mesylate.

20. A method of claim 17 wherein the xanthine is of formula

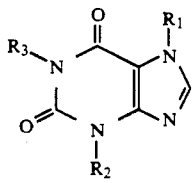

I wherein $R_1$, $R_1$ and $R_3$ are chosen from hydrogen or alkyl($C_{1-10}$).

21. A method of claim 20 wherein the xanthine is theophylline.

22. A method of claim 20 wherein the xanthine is caffeine.

23. A method of claim 20 wherein from 2 to 20 mg of xanthine per dose is administered.

24. A method according to claim 17 wherein a spray of liquid is administered.

25. A method according to claim 24 wherein the osmotic pressure of the liquid is 280 to 360 mOsm per liter.

26. A method according to claim 17 wherein a spray of powder is administered.

27. A method according to any one of claims 17 wherein a non-toxic isotonizing agent is also co-administered.

28. A method according to claim 27 wherein the isotonizing agent is a sugar.

29. A method according to claim 28 wherein the sugar is glucose.

30. A method according to claim 29 wherein the dose of sugar is from about 10 to 100 mg.

31. A method according to any one of claims 17 wherein the dose of dihydroergotamine administered is from 0.5 to 5 mg.

* * * * *